United States Patent [19]

MacFadden

[11] 4,207,396
[45] * Jun. 10, 1980

[54] CELLULOSE FERMENTATION PROCESS

[75] Inventor: Donald L. MacFadden, Bristol, Tenn.

[73] Assignee: Chevron Research Company, San Francisco, Calif.

[*] Notice: The portion of the term of this patent subsequent to Jul. 18, 1995, has been disclaimed.

[21] Appl. No.: 902,571

[22] Filed: May 4, 1978

Related U.S. Application Data

[62] Division of Ser. No. 801,933, May 31, 1977, Pat. No. 4,101,679.

[51] Int. Cl.² .................................................. A23K 1/12
[52] U.S. Cl. ..................................... 435/244; 435/252; 426/53; 426/807; 424/273 R
[58] Field of Search .................... 195/33, 96, 114, 121, 195/122, 123; 424/273 R; 548/311

[56] References Cited

U.S. PATENT DOCUMENTS 3,178,447 4/1965 Kohn ...................................... 548/311
3,314,969 4/1967 Flay ...................................... 548/311

OTHER PUBLICATIONS

O'Connor et al., "Chemical Additives in Rumen Fermentations", Journal of Animal Science, vol. 33, pp. 662–666 (1971).

Hajny et al., "Cellulose and Their Applications", American Chemical Society Publishing Co., pp. 415–421 (1969).

Primary Examiner—R. B. Penland
Attorney, Agent, or Firm—D. A. Newell; T. G. DeJonghe; R. J. Suyat

[57] ABSTRACT

In vivo and in vitro cellulose fermentation by cellulose-digesting microorganisms is increased by conducting the fermentation in the presence of a minor amount of a compound of the formula

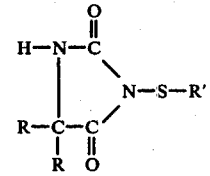

wherein R' is haloalkyl and R is H or alkyl.

6 Claims, No Drawings

CELLULOSE FERMENTATION PROCESS

This is a division of application Ser. No. 801,933 filed May 31, 1977 now U.S. Pat. No. 4,101,679.

BACKGROUND OF THE INVENTION

The effect of chemical additives in microorganism fermentations has been extensively studied. For example, P. P. Williams et al, App. Microbiology, 11, 517 (1963) describe rumen bacterial and protozoal responses to insecticide substrate; J. J. O'Connor et al, J. Animal Sci., 33, 662 (1970) describe the in vivo effect of chemical additives on production of volatile fatty acids by rumen microorganisms; L. W. Varner et al, J. Animal Sci., 33, 1110 (1971), describe the influence of ammonium salts upon rumen fermentation by steers; and T. W. Dowe et al, J. Animal Sci., 16, 93 (1957) describe the effect of corn treated with fungicides (N-trichloromethylthio-delta$^4$-tetrahydrophthalimide) upon the performance of fattening steers.

DESCRIPTION OF THE INVENTION

Cellulose-Fermentation-Accelerating-Compounds

The cellulose-fermentation-accelerating compounds of the invention are represented by the formula

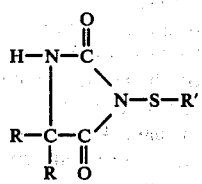

wherein R' is haloalkyl of 1 to 2 carbon atoms and 1 to 5 chloro or bromo groups and R individually is hydrogen or lower alkyl of 1 to 6 carbon atoms.

The compounds of Formula (I) are 3-haloalkylthiohydantoins, 3-haloalkylthio-5-alkylhydantoins and 3-haloalkylthio-5,5-dialkylhydantoins, wherein the haloalkyl group (R') and the alkyl (R) group are as defined above.

Preferably R' is chloroalkyl of 1 to 2 carbon atoms and 11.5 chloro groups, especially trichloromethyl or tetrachloroethyl. Preferably, both R groups are alkyl, especially alkyl of 1 to 3 carbon atoms, such as methyl.

Representative hydantoin compounds of Formula I are:
3-trichloromethylthiohydantoin
3-(1,1,2,2-tetrachloroethylthio) hydantoin
3-trichloromethylthio-5-amylhydantoin
3-trichloromethylthio-5-methylhydantoin
3-(1,1,2,2-tetrachloroethylthio)-5-methyl-5-amylhydantoin
3-trichloromethyl-5,5-dimethylhydantoin.

The amount of compound employed in the process of the application depends in part upon the type of cellulosic material and the particular microorganism (s) employed. Generally, weight ratios of compounds of cellolosic matter in the range of about 1:10 to 1:1,000,000 are effective, although weight ratios in the range of about 1:100 to 1:10,000 are preferred.

In in vitro cellulose fermentation processes, the compound is generally added directly to the fermentation process. In in vivo cellulose digestion, the compound may be orally administered to the animal along with the cellulosic feedstuff. Alternatively, the cellulosic feedstuff may be pre-treated with an effective amount of the complound prior to feeding the animal.

Cellulose Fermentation Process

The process of the invention is generally applicable to in vivo or in vitro cellulose fermentation by microorganisms. Examples of in vitro cellulose fermentation by microorganisms are the aerobic and/or anerobic destruction of cellulosic wastes in sewage plants; conversion of cellulose to sugar by microorganisms such as *Trichoderma viride;* conversion of cellulose to single-cell proteins by microorganisms such as *Bacteroidaceae, Cellulomonas* and *Alcaliginis;* and the biodegradation of lignincellulosic plant material. Examples of in vivo fermentation by microorganisms are cellulosic digestion by rumen microorganisms (e.g., *Bacterioides succinogenes* and *Ruminococcus albus*) of ruminant animals, cecum microorganisms of animal intestines, and other cellulolytic organisms in the alimentary tracts of herbivores.

The process of the invention is suitably employed for all types of cellulosic material such as paper, municipal waste and plant products, e.g., wood, cotton, straw, bagasse, rice hulls, etc.

EXAMPLES

EXAMPLE 1—COTTON DIGESTION BY BACTEROIDES SUCCINOGENES

The organism *Bacteroides succinogenes* was obtained from the American Type Culture Collection, No. 19169.

| Nutrient Source: | Bacto-fluid Thioglycollate (29 g formulation/liter of H$_2$O) |
| --- | --- |
| Bacto-Casitone | 15.0 g |
| Bacto-Yeast Extract | 5.0 g |
| Bacto-Dextrose | 5.0 g |
| NaCl | 2.5 g |
| 1-Cystine, Difco | 0.5 g |
| Thioglycolic Acid | 0.3 ml |
| Bacto-Agar Resazurin, Certified | 0.001 g |

The rate of cotton digestion in the presence of 3-(trichloromethylthio) 5,5-dimethylhydantoin in the above nutrient broth with *Bacteroides succinogenes* was determined by the following procedure:

Cotton (100 mg) was placed in screw-cap tubes. To these the test compound (1 microgram) and the nutrient source (20 ml) were added to completely fill the tube.

The tubes were then sterilized, cooled and inoculated with the microbe (1 loop of inoculation needle), their caps tightened, and incubated in a water bath at about 40° C.

The tubes were stirred throughout incubation and the caps loosened every 2 hours for the first 18 hours and every 6 hours thereafter to release gases produced by the fermentation. After 70 hours of incubation, most of the fermentation processes had subsided, as noted by cessation of gas accumulation.

After various periods of incubation, the tubes were emptied on previously weighed filter paper. The filter paper was washed several times and dried to a constant weight. The weight of the undigested cotton was determined by difference.

The cellulose digestion results are tabulated in Table I. The results are based on the average of 40–100 runs and standard deviation analysis showed the results to be significant at the 1% level.

TABLE I

| Time (Hr) | Cotton Digestion (in mg) | |
| --- | --- | --- |
| | Control | Test Compound |
| 10 | 0 | 0 |
| 20 | 0.5 | 0.5 |
| 30 | 1.5 | 2.5 |
| 40 | 3.5 | 6.5 |
| 50 | 16.0 | 22.5 |
| 60 | 30.0 | 38.5 |
| 70 | 37.5 | 44.0 |

EXAMPLE 2—COTTON DIGESTION BY BACTEROIDES SUCCINOGENES

The rate of cotton digestion with *Bacteroides succinogenes* in the presence of 3-(1,1,2,2-tetrachloroethylthio)-5,5-dimethylhydantoin was determined by a procedure similar to that of Example 1, except that the incubation period was 8 days and no stirring was employed. The results are tabulated in Table II.

TABLE II

| Concentration* of Test Compound | Total mg Cellulose Digested |
| --- | --- |
| 0 | 90 (control) |
| 100 | 102.5 |
| 500 | 172.5 |
| 1000 | 187.5 |

*micrograms

What is claimed is:

1. A method for accelerating the rate of cellulose fermentation by cellulose-digesting microorganisms which comprises conducting said fermentation in the presence of a rate-accelerating amount of a compound of the formula

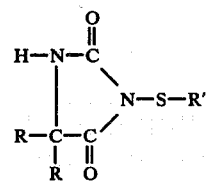

wherein R' is haloalkyl of 1 to 2 carbon atoms and 1 to 5 chloro or bromo groups and R individually is hydrogen or lower alkyl of 1 to 6 carbon atoms.

2. The method of claim 1 wherein both R groups are lower alkyl and R' in chloroalkyl of 1 to 2 carbon atoms and 1 to 5 chloro groups.

3. The method of claim 1 wherein both R groups are methyl and R' is trichloromethyl.

4. The method of claim 1 wherein both R groups are methyl and R' tetrachloroethyl.

5. The method of claim 1 wherein both R groups are methyl and R' is 1,1,2,2-tetrachloroethyl.

6. The method of claim 1 wherein the cellulose is cellulosic waste products.

* * * * *

UNITED STATES PATENT AND TRADEMARK OFFICE
CERTIFICATE OF CORRECTION

PATENT NO. : 4,207,396
DATED : June 10, 1980
INVENTOR(S) : Donald L. MacFadden

It is certified that error appears in the above-identified patent and that said Letters Patent are hereby corrected as shown below:

Col. 1, lines 60-61, "cellolosic" should read --cellulosic--.

Col. 4, line 27, "in" should read --is--.

Col. 4, line 32, "R'" should read --R' is--.

Signed and Sealed this

Twenty-third Day of September 1980

[SEAL]

Attest:

SIDNEY A. DIAMOND

Attesting Officer

Commissioner of Patents and Trademarks